(12) United States Patent
Foy et al.

(10) Patent No.: US 6,413,420 B1
(45) Date of Patent: Jul. 2, 2002

(54) MAGNETIC SEPARATION DEVICE

(75) Inventors: Jeffrey E. Foy, San Jose; Eric B. Sweeney, Fremont, both of CA (US)

(73) Assignee: Dexter Magnetic Technologies, Inc., Fremont, CA (US)

( * ) Notice: Subject to any disclaimer, the term of this patent is extended or adjusted under 35 U.S.C. 154(b) by 0 days.

(21) Appl. No.: 09/527,797

(22) Filed: Mar. 17, 2000

(51) Int. Cl.$^7$ .......................... G01N 33/553; C12M 1/00
(52) U.S. Cl. .......................... 210/222; 210/94; 210/95; 436/526; 436/534; 436/806; 435/173.1; 335/302; 335/306
(58) Field of Search .................... 210/222, 695, 210/94, 95; 209/2, 3; 435/173.1; 436/526, 534, 806; 335/302, 306

(56) References Cited

U.S. PATENT DOCUMENTS 4,710,472 A * 12/1987 Saur et al. ................. 210/222

5,466,574 A   11/1995 Liberti et al.

\* cited by examiner

Primary Examiner—David A. Reifsnyder
(74) Attorney, Agent, or Firm—Blakely Sokoloff Taylor & Zafman

(57) ABSTRACT

A magnetic biological particle separation device comprising a permanent magnet structure substantially surrounding a vessel containing a liquid and a biological sample in colloidal suspension in the liquid is described. The magnetic separation device comprises a window through which to view the liquid. The permanent magnet structure comprises a plurality of permanent magnets arranged in such a manner to provide for superpositioning of the external magnetic field generated by each magnet. The external magnetic field acts on magnetic beads attached to the biological sample, causing the sample to move toward the inner wall of the vessel. The permanent magnets do not completely surround the outside of the vessel to allow the liquid to be poured out of the vessel, substantially leaving the sample.

11 Claims, 2 Drawing Sheets

MAGNETIC SEPARATION DEVICE

BACKGROUND OF THE INVENTION

1. Field of the Invention

The present invention relates to a an arrangement of permanent magnets that separates particles from a solution in a vessel, as utilized in the field of biology to remove cells from a sample contained in a test tube or the like.

2. Description of the Related Art

Copending patent application 08/868,598, filed in the U.S. Patent and Trademark Office on Jun. 4, 1997 still pending, describes a magnetic device that surrounds a vessel, such as a test tube, containing a liquid sample. The liquid sample may be a colloidal suspension or at least a fluid mixture. The magnetic device provides an external magnetic field within a liquid sample for the purpose of causing separation of magnetized particles or cells from the liquid sample. The magnetic device has four polar magnets and a plurality of interpolar magnets positioned to provide an external magnetic field having a high flux density gradient within the liquid sample. However, the uniform magnetic field gradient generated within the liquid sample impedes the ability to easily pour off the liquid after a significant amount of cell separation has occurred, without suffering the loss of magnetized particles as well. Moreover, the magnet structure, in surrounding the vessel, fails to provide a viewing window through which to view the liquid sample, for example, to detect the degree of separation of the magnetized particles from the liquid sample.

BRIEF SUMMARY OF THE INVENTION

An apparatus for biological particle separation, comprising a vessel containing a plurality of biological particles suspended in a liquid. The vessel has a proximate open end, and a distal closed end. A number of magnetic beads are biologically attached to the biological particles. The beads, generally spherical, may range from 50 nanometers to 10 microns mean diameter. The magnet structure substantially surrounds all but a portion of a wall of the vessel to draw the particles to the wall of the vessel and allow the liquid to be poured off via the portion of the wall not surrounded by the magnet structure, without losing the magnetic beads and particles attached thereto.

BRIEF DESCRIPTION OF THE SEVERAL VIEWS OF THE DRAWINGS

The embodiments of the present invention are illustrated by way of example and not limitation in the accompanying figures, in which.

DETAILED DESCRIPTION OF THE INVENTION

Figure 1:
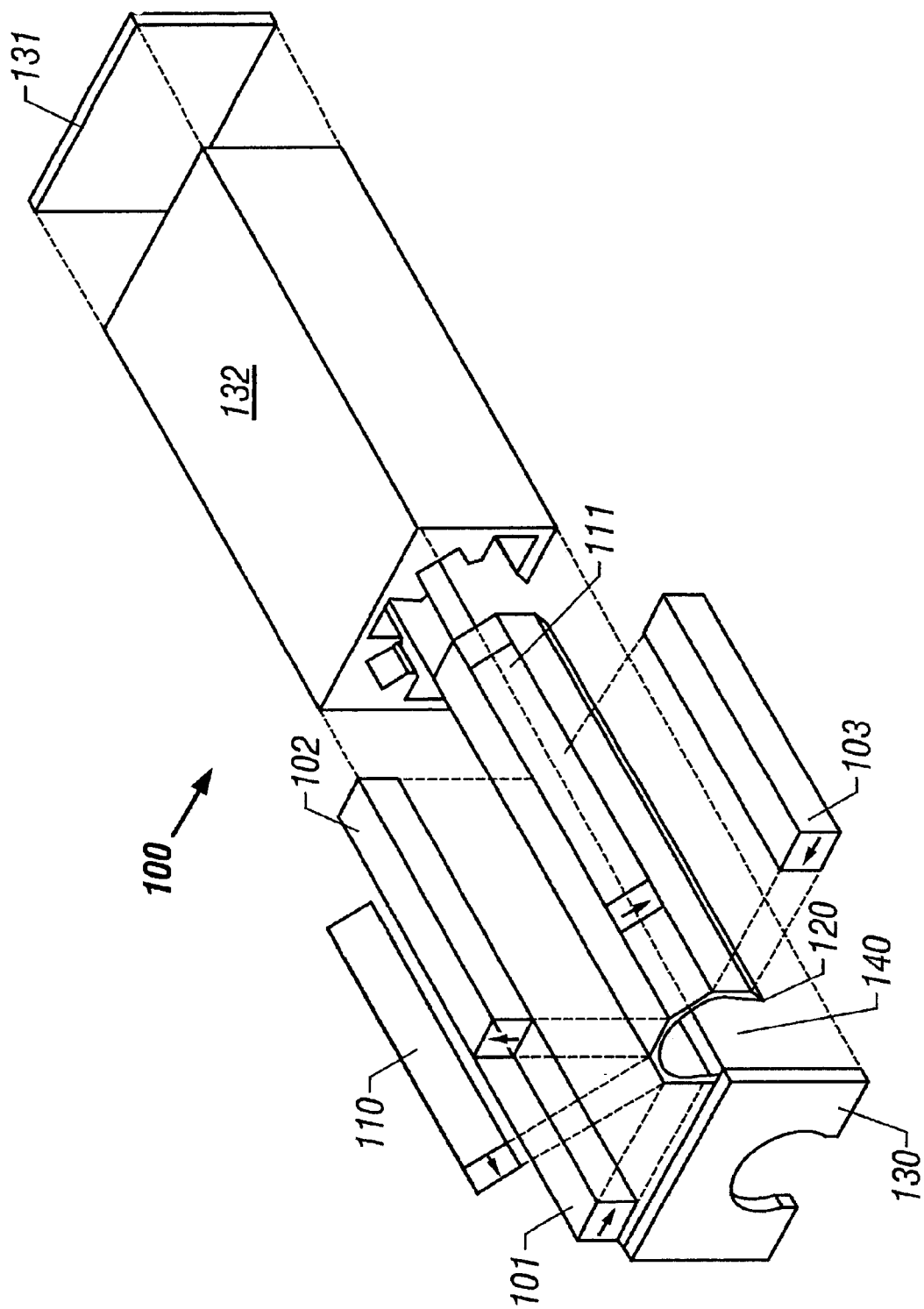
FIG. 1 provides a three dimensional view of an embodiment of the present invention.
Figure 2:
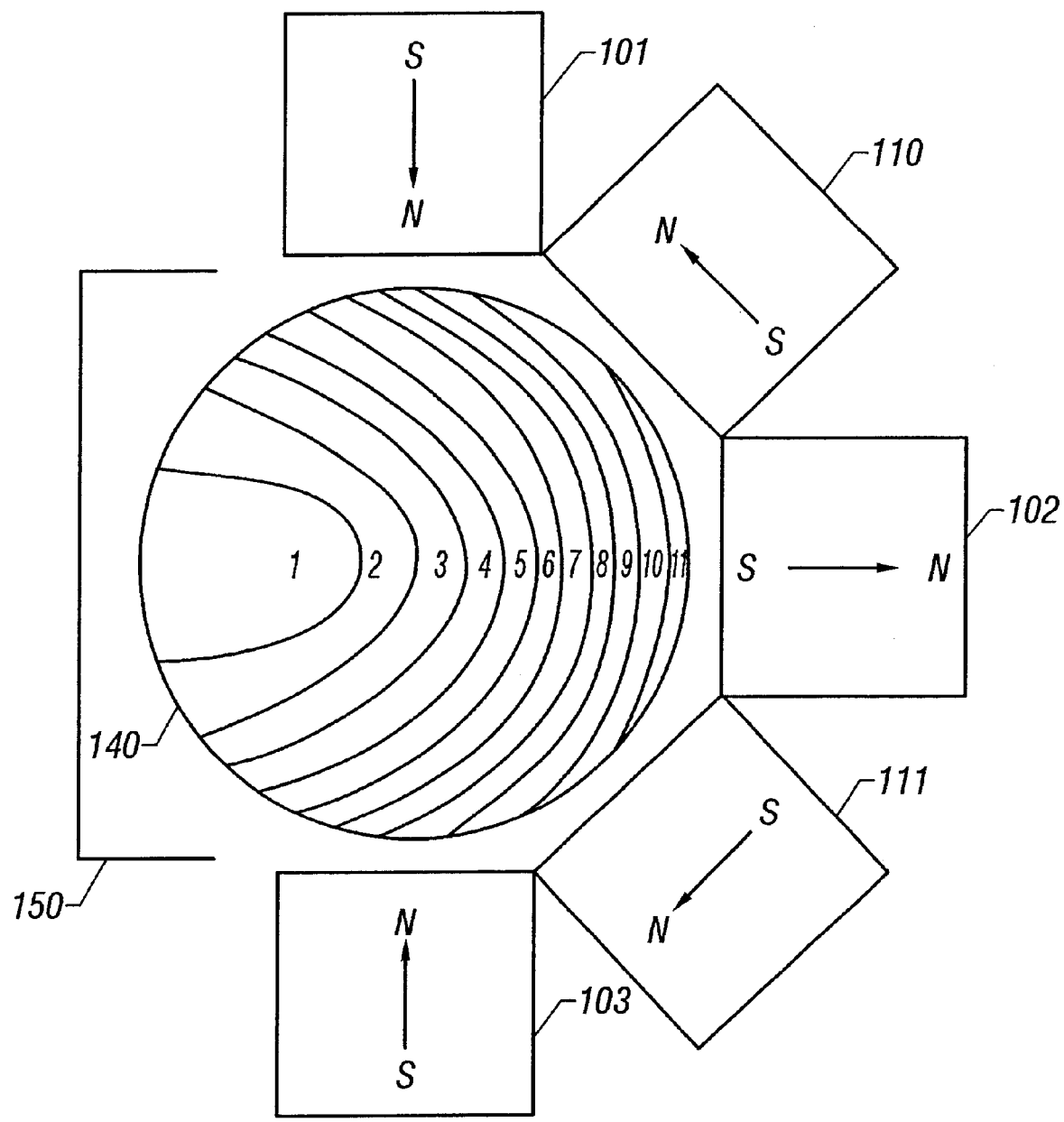
FIG. 2 provides a cross sectional view of an embodiment of the present invention.

An embodiment 100 of the present invention is described with reference to FIGS. 1 and 2. Three dipole permanent magnets 101, 102 and 103 are mounted proximate a non-magnetic shell 120. Magnets 101 and 103 are termed herein as north polar magnets because they are dipole magnets with their north pole directed radially, inward toward an aperture or gap 140. Magnet 102 is termed herein a south polar magnet given that its south pole is directed inward toward the gap 140. A vessel, such a test tube (not shown) may be inserted into the gap so that the external magnetic field generated by the magnet structure 100 may act upon the contents of the vessel in the manner described herein below.

A number of bucking magnets, termed herein interpolar magnets 110 and 111, are situated between the polar magnets as illustrated, to complete a magnetic circuit between the polar magnets. In other words, the magnetic field orientation of the interpolar magnets is situated essentially perpendicular the apertur to best facilitate a magnetic circuit between the polar magnets. The superpositioning of the magnetic fields of the polar and interpolar magnets provides maximum external field strength for the given magnetic material utilized in the magnet structure 100.

The magnet structure 100 is utilized in an embodiment of the present invention to separate a magnetized substance from a non-magnetized substance. For example, in the field of biology, it may be desired to separate a particle, cell, nucleic acid or DNA molecule from another substance such as a bodily fluid or substance. The separation of the magnetized substance may be for diagnostic or testing purposes, or for harvesting a particular substance for therapeutic purposes.

The magnetic structure 100, with its combination of polar magnets, and interpolar magnets positioned therebetween, creates an external magnetic field of maximum field strength and gradient in the aperture 140. More specifically, the structure provides for a substantially uniform flux gradient over a liquid sample in a vessel placed within aperture 140.

The magnetic structure is illustrated as having three polar magnets with interpolar magnets adjacent the polar magnets. However, it is appreciated that more or less polar and interpolar magnets may be utilized to form a partially enclosed aperture 140 in which a vessel comprising a liquid may be placed. It is further appreciated that a single magnet with a multipole magnetization may be utilized. The substantially uniform external magnetic field gradient illustrated in FIG. 2 provides radial movement of magnetized particles in the fluid to the inner wall of the vessel other than to that part of the wall of the vessel through which is provided a viewing window. Additionally, the aperture, and vessel, while illustrated herein as forming a cylinder, it is appreciated that other polygonal shapes may be utilized, ranging from smooth uniform circular shapes to irregular, multidimensional, multisided shapes, the primary point being that the aperture accommodate insertion of a vessel such as a test tube containing a liquid sample. Moreover, the closer the magnetic structure to the vessel, and the thinner the vessel, the more efficient the external magnetic field is in separating the sample from the liquid.

The magnets may be comprised of iron, nickel, cobalt, and rare earth materials such as neodymium and samarium, or combinations or derivatives thereof, such as neodymium iron boron. These and other high coercivity materials with an intrinsic coercivity greater than the flux density provided by the magnetic structure may be used.

The portion of the aperture providing for a viewing window 150 serves another important purpose. Separation of the biological material from suspension in the liquid sample is facilitated by the magnetic'structure. Upon sufficient separation, the liquid needs to be removed to recover the sample. In the embodiment of the present invention, the liquid is removed by pouring the liquid from the vessel while the vessel remains in the aperture 140. When separating the liquid from the sample by pouring, care must be taken to minimize sample loss when the fluid flows over the magnetic beads and particles attached thereto. Thus, there must be a sufficient arc on the vessel where no magnetized particles collect on the inner wall. The biological sample with embedded magnetic beads, under the force applied by the external magnetic field, gathers along the inner walls of vessel other than at that portion of the vessel through which the viewing window is provided. Thus, the liquid may be poured out from the open proximate end of the vessel by tipping the open end of the vessel in the direction of the viewing window 150.

In one embodiment of the present invention, the magnetic structure extends no more than 270 degrees around the vessel, thus providing a "no separation zone". This zone where no particles collect is the portion of the vessel over which the sample is viewed and liquid is poured to separate the liquid from the magnetized biological sample. In alternative embodiments, the magnetic structure extends perhaps 300 degrees or more, or a little as 180 degrees, to provide more or less viewing window, pouring capability, and rate of sample separation.

What is claimed is:

1. A magnetic arrangement comprising:

a first magnet to generate a first north-south magnetic field in a plane co-planer with a horizontal cross-sectional plane of a container;

a second magnet to generate a second north-south magnetic field substantially opposing the first north-south magnetic field in a plane co-planer with the horizontal cross-sectional plane of a container;

a third magnet to generate a third north-south magnetic field substantially perpendicular to the first and second north-south magnetic fields, directed radially away from the container, in a plane co-planar with the horizontal cross-sectional plane of the container; and a fourth magnet between the first and third magnet, to generate a fourth north-south magnetic field in a plane co-planar with the first north-south magnetic field, and directed away from the third magnet toward the first north-south magnetic field, the magnet arrangement to allow a fluid containing magnetic beads within the container to be poured from the container without a substantial loss of the magnetic beads.

2. The magnet arrangement of claim 1 further comprising a viewing window to view separation of the magnetic beads within the container.

3. The magnet arrangement of claim 1 further comprising a fifth magnet, between the second and third magnet, to generate a fifth north-south magnetic field in a plane coplanar with the first north-south magnetic field, and directed toward the second north-south magnetic field.

4. The magnet arrangement of claim 3 wherein the magnets are permanent magnets.

5. The magnet arrangement of claim 3 wherein the first, second, third, fourth, and fifth magnetic fields extend for substantially the length of the container.

6. The magnet arrangement of claim 1 wherein the container contains biological particles.

7. The container of claim 6 wherein the biological particles comprise biological cells.

8. The container of claim 6 wherein the biological particles comprise molecular components.

9. The container of claim 6 wherein the biological particles are suspended in a liquid.

10. The magnet arrangement of claim 1 wherein the container is any one of a test tube, a bottle, a beaker and a tube.

11. The magnetic arrangement of claim 1 wherein the container contains a plurality of magnetic beads.

* * * * *